United States Patent

Joshi et al.

[11] Patent Number: 5,180,589
[45] Date of Patent: * Jan. 19, 1993

[54] PRAVASTATIN PHARMACEUATICAL COMPOSITIONS HAVING GOOD STABILITY

[75] Inventors: Yatindra M. Joshi, Piscataway; Pierina Chiesa, South Orange; Nemichand B. Jain, Monmouth Junction, all of N.J.

[73] Assignee: E. R. Squibb & Sons, Inc., Princeton, N.J.

[ * ] Notice: The portion of the term of this patent subsequent to Jul. 9, 2008 has been disclaimed.

[21] Appl. No.: 703,326

[22] Filed: May 20, 1991

Related U.S. Application Data

[63] Continuation of Ser. No. 176,127, Mar. 31, 1988, Pat. No. 5,030,447.

[51] Int. Cl.⁵ .......................... A61K 9/14; A61K 9/20
[52] U.S. Cl. .............................. 424/465; 424/464; 424/489; 514/510; 514/548; 514/970; 560/119
[58] Field of Search ................ 424/80, 464, 465, 470, 424/474

[56] References Cited

U.S. PATENT DOCUMENTS

| | | | |
|---|---|---|---|
| 3,865,935 | 2/1975 | Amann | 424/181 |
| 3,891,755 | 6/1975 | Mehta | 424/157 |
| 3,983,140 | 9/1976 | Endo et al. | 435/72 |
| 4,342,767 | 8/1982 | Albers-Schonberg et al. | 424/250 |
| 4,346,227 | 8/1982 | Terahara et al. | 560/119 |
| 4,609,675 | 9/1986 | Franz | 514/568 |
| 4,681,759 | 7/1987 | Porubcan | 424/80 |
| 4,755,385 | 7/1988 | Etienne et al. | 424/154 |
| 5,030,447 | 7/1991 | Joshi et al. | 424/80 |

Primary Examiner—Thurman K. Page
Assistant Examiner—James M. Spear
Attorney, Agent, or Firm—Burton Rodney

[57] ABSTRACT

A pharmaceutical composition is provided which has excellent stability, when dispersed in water has a pH of at least about 9, and includes a medicament which is sensitive to a low pH environment such as pravastatin, one or more fillers such as lactose and/or microcrystalline cellulose, one or more binders, such as microcrystalline cellulose (dry binder) or polyvinylpyrrolidone (wet binder), one or more disintegrating agents such as croscarmellose sodium, one or more lubricants such as magnesium stearate and one or more basifying agents such as magnesium oxide.

12 Claims, No Drawings

PRAVASTATIN PHARMACEUATICAL COMPOSITIONS HAVING GOOD STABILITY

This is a continuation of application Ser. No. 176,127, filed Mar. 31, 1988, now U.S. Pat. No. 5,030,447.

FIELD OF THE INVENTION

The present invention relates to a pharmaceutical composition, preferably in the form of a tablet, which includes a medicament which is sensitive to a low pH environment, such as pravastatin, yet has excellent stability.

BACKGROUND OF THE INVENTION

Pharmaceutical compositions which include a medicament which is unstable in an acidic environment will require a basic excipient to enhance storage stability.

Pravastatin, an HMG-CoA reductase inhibitor disclosed in U.S. Pat. No. 4,346,227 to Terahara et al and having the formula

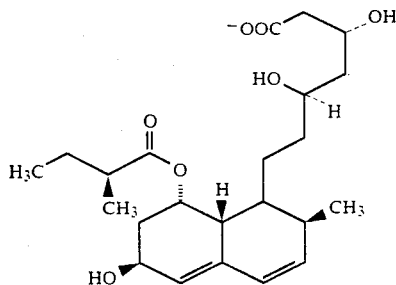

is sensitive to a low pH environment and will degrade to form its lactone and various isomers.

DESCRIPTION OF THE INVENTION

In accordance with the present invention, a pharmaceutical composition is provided which has excellent storage stability even though it includes a medicament which may degrade in a low pH environment. The pharmaceutical composition of the invention, which is preferably in the form of a tablet, includes a medicament which is sensitive to a low pH environment, such as pravastatin, one or more fillers, such as lactose and/or microcrystalline cellulose, one or more binders, such as mirocrystalline cellulose (dry binder) or polyvinylpyrrolidone (wet binder), one or more disintegrating agents such as croscarmellose sodium, one or more lubricants such as magnesium stearate, and one or more basifying agents such as magnesium oxide to impart a pH to an aqueous dispersion of the composition of at least about 9.0.

The invention is particularly adapted to pharmaceutical compositions containing pravastatin as the medicament. Pravastatin, will be present in an amount within the range of from about 1 to about 60% and preferably from about 3 to about 50% by weight of the composition.

To ensure acceptable stability, the composition of the invention will include a basifying agent which will raise the pH of an aqueous dispersion of the composition to at least 9 and preferably to a pH of at least about 9.5. The basifying agent will be present in an amount within the range of from about 1 to about 75% by weight and preferably from about 2 to about 70% by weight of the composition. Examples of basifying agents which may be included herein include but are not limited to magnesium oxide, aluminum oxide, an alkali metal hydroxide such as sodium hydroxide, potassium hydroxide or lithium hydroxide or an alkaline earth metal hydroxide such as calcium hydroxide or magnesium hydroxide, with magnesium oxide being preferred.

The composition of the invention will also include one or more fillers or excipients in an amount within the range of from about 5 to about 90% by weight and preferably from about 10 to about 80% by weight such as lactose, sugar, corn starch, modified corn starch, mannitol, sorbitol, inorganic salts such as calcium carbonate and/or cellulose derivatives such as wood cellulose and microcrystalline cellulose.

One or more binders will be present in addition to or in lieu of the fillers in an amount within the range of from about 5 to about 35% and preferably from about 10 to about 30% by weight of the composition. Examples of such binders which are suitable for use herein include polyvinylpyrrolidone (molecular weight ranging from about 5000 to about 80,000 and preferably about 40,000), lactose, starches such as corn starch, modified corn starch, sugars, gum acacia and the like as well as a wax binder in finely powdered form (less than 500 microns) such as carnauba wax, paraffin, spermaceti, polyethylenes or microcrystalline wax.

Where the composition is to be in the form of a tablet, it will include one or more tablet disintegrants in an amount within the range of from about 0.5 to about 10% and preferably from about 2 to about 8% by weight of the composition such as croscarmellose sodium, crospovidone, sodium starch glycolate, corn starch or microcrystalline cellulose as well as one or more tableting lubricants in an amount within the range of from about 0.2 to about 8% and preferably from about 0.5 to about 2% by weight of the composition, such as magnesium stearate, stearic acid, palmitic acid, calcium stearate, talc, carnauba wax and the like. Other conventional ingredients which may optionally be present include preservatives, stabilizers, anti-adherents or silica flow conditioners or glidants, such as Syloid brand silicon dioxide as well as FD&C colors.

Tablets of the invention may also include a coating layer which may comprise from 0 to about 15% by weight of the tablet composition. The coating layer which is applied over the tablet core may comprise any conventional coating formulations and will include one or more film-formers or binders, such as a hydrophilic polymer like hydroxypropylmethyl cellulose and a hydrophobic polymer like ethyl cellulose, cellulose acetate, polyvinyl alcohol-maleic anhydride copolymers, β-pinene polymers, glyceryl esters of wood resins and the like and one or more plasticizers, such as triethyl citrate, diethyl phthalate, propylene glycol, glycerin, butyl phthlate, castor oil and the like. Both core tablets as well as coating formulations may contain aluminum lakes to provide color.

The film formers are applied from a solvent system containing one or more solvents including water, alcohols like methyl alcohol, ethyl alcohol or isopropyl alcohol, ketones like acetone, or ethylmethyl ketone, chlorinated hydrocarbons like methylene chloride, dichloroethane, and 1,1,1-trichloroethane.

Where a color is employed, the color will be applied together with the film former, plasticizer and solvent compositions.

A preferred tablet composition of the invention will include from about 2 to about 35% by weight pravastatin, from about 2.5 to about 70% by weight magnesium oxide, from about 10 to about 80% by weight lactose, from about 10 to about 30% by weight microcrystalline cellulose or polyvinylpyrrolidone, from about 2 to about 8% by weight croscarmellose sodium and from about 0.5 to about 2% by weight magnesium stearate.

The pharmaceutical composition of the invention may be prepared as follows. A mixture of the medicament (pravastatin), basifying agent (preferably magnesium oxide), and a fraction (less than 50%) of the filler (such as lactose), with or without color, are mixed together and passed through a #12 to #40 mesh screen. Filler-binder (such as microcrystalline cellulose), disintegrant (such as croscarmellose sodium) and the remaining lactose are added and mixed. Lubricant (such as magnesium stearate) is added with mixing until a homogeneous mixture is obtained.

The resulting mixture may then be compressed into tablets of up to 1 gram in size Where desired, the tablets of the invention may be formulated by a wet granulation technique wherein medicament (pravastatin) is dissolved in warm aqueous solution of binder (polyvinylpyrrolidone). The resulting solution is used to granulate a mixture of filler (lactose hydrous), basifying agent (such as magnesium oxide), filler-binder (microcrystalline cellulose), and a portion of the disintegrant (croscarmellose sodium). The granulated mixture is passed through a #4 to #10 mesh screen and is then dried in a tray drying oven. The dried granulation is passed through a #12 to #20 mesh screen. The remainder of the disintegrant and the lubricant (such as magnesium stearate) are added and the resulting granules are compressed into a tablet.

The tablets may also be formulated by a wet granulation technique where a mixture of the medicament (pravastatin), basifying agent (preferably magnesium oxide), filler-binder (such as microcrystalline cellulose), and a fraction (less than 50%) of the filler (such as lactose) with or without color, are mixed and passed through a #12 to #40 mesh screen. A portion of the disintegrant (such as croscarmellose sodium) and the remaining lactose are added and mixed. The resulting mixture is granulated using an aqueous binder solution (such as polyvinyl pyrrolidone). The formulated wet mixture is passed thorugh a #4 to #20 mesh screen and is then dried in a tray drying oven. The dry granulation is passed through a #12 to #20 mesh screen. The remainder of the disintegrant and the lubricant (such as magnesium stearate) are added and the resulting granules are compressed into a tablet.

All mesh sizes are U.S. Standard ASTME.

The following Examples represent preferred embodiments of the present invention. All temperatures are expressed in degrees Centigrade unless otherwise indicated and all mesh sizes are U.S. Standard ASTME.

EXAMPLE 1

A pravastatin formulation in the form of tablets having the following composition was prepared as described below.

| Ingredient | Percent by Weight |
| --- | --- |
| Pravastatin | 6.7 |
| Lactose | 67 |
| Microcrystalline cellulose | 20 |
| Croscarmellose sodium | 2 |
| Magnesium stearate | 1 |
| Magnesium oxide | 3.3 |

Pravastatin, magnesium oxide and a fraction (30%) of the lactose were mixed together for 2 to 10 minutes employing a suitable mixer. The resulting mixture was passed through a #12 to #40 mesh size screen. Microcrystalline cellulose, croscarmellose sodium and the remaining lactose were added and the mixture was mixed for 2 to 10 minutes. Thereafter, magnesium stearate was added and mixing was continued for 1 to 3 minutes.

The resulting homogeneous mixture was then compressed into tablets each containing 5 mg, 10 mg, 20 or 40 mg pravastatin.

A dispersion of the tablets in water had a pH of about 10.

Upon subjecting the so-formed tablets to a stability study at 60° C., or 40° C./75% relative humidity for 2 months, it was found that the tablets including the pravastatin remained substantially stable; no lactone formation was observed.

EXAMPLE 2

A pravastatin formulation in the form of tablets, each containing 5 mg, 10 mg, 20 mg or 40 mg pravastatin, having the following composition was prepared as described in Example 1, except that color was incorporated into the powder mixture containing pravastatin, magnesium oxide and a fraction of the lactose.

| Ingredient | Percent by Weight |
| --- | --- |
| Pravastatin | 6.7 |
| Lactose | 66.8 |
| Microcrystalline cellulose | 20 |
| Croscarmellose sodium | 2 |
| Magnesium stearate | 1 |
| Magnesium oxide | 3.3 |
| FD&C Red #3 Lake | 0.2 |

A dispersion of the tablets in water had a pH of about 10.

Upon subjecting the so-formed tablets to a stability study at 60° C., or 40° C./75% relative humidity for 2 months, it was found that the tablets including the pravastatin remained substantially stable; no lactone formation was observed.

EXAMPLE 3

A pravastatin formulation in the form of tablets, each containing 5 mg, 10 mg, 20 mg or 40 mg pravastatin, having the following composition was prepared as described below.

| Ingredient | Percent by Weight |
| --- | --- |
| Pravastatin | 6.7 |
| Lactose | 71 |
| Microcrystalline cellulose | 15 |
| Croscarmellose sodium | 2 |
| Magnesium stearate | 1 |
| Magnesium oxide | 3.3 |
| Polyvinylpyrrolidone | 1 |

Pravastatin was dissolved in warm aqueous solution of polyvinylpyrrolidone. The solution was used to granulate a mixture of lactose, magnesium oxide, microcrystalline cellulose and a fraction of the croscarmellose sodium. The formulated mixture was passed through a #4 to #10 mesh screen and was then dry granulated in a tray drying oven. The dry granulation was passed through a #12 to #20 mesh screen. The remainder of the disintegrant was added to the dry granules and mixed for 2 to 10 minutes. Thereafter, magnesium stearate was added and mixing was continued for 1 to 5 minutes. The resulting granulation was compressed into tablets.

A dispersion of the tablets in water had a pH of about 10.

Upon subjecting the so-formed tablets to a stability study at 60° C. or 40° C./75% relative humidity for 2 months, it was found that the tablets including the pravastatin remained substantially stable; no lactone formation was observed.

EXAMPLE 4

A pravastatin formulation in the form of tablets, each containing 5 mg, 10 mg, 20 mg or 40 mg pravastatin, having the following composition was prepared as described in Example 3, except that color was incorporated into the powder mixture containing lactose, magnesium oxide, microcrystalline cellulose and a fraction of the croscarmellose sodium

| Ingredient | Percent by Weight |
| --- | --- |
| Pravastatin | 6.7 |
| Lactose | 70.8 |
| Microcrystalline cellulose | 15 |
| Croscarmellose sodium | 2 |
| Magnesium stearate | 1 |
| Magnesium oxide | 3.3 |
| FD&C #3 Lake | 0.2 |
| Polyvinylpyrrolidone | 1 |

A dispersion of the tablets in water had a pH of about 10.

Upon subjecting the so-formed tablets to a stability study at 60° C. or 40° C./75% relative humidity for 2 months, it was found that the tablets including the pravastatin remained substantially stable; no lactone formation was observed.

EXAMPLE 5

A pravastatin formulation in the form of tablets, each containing 10 mg pravastatin, having the following composition was prepared as described in Example 3.

| Ingredient | Percent by Weight |
| --- | --- |
| Pravastatin | 6.7 |
| Lactose | 54.5 |
| Polyvinylpyrrolidone | 0.5 |
| Croscarmellose sodium | 4 |
| Magnesium stearate | 1 |
| Magnesium oxide | 33.3 |

A dispersion of the tablets in water had a pH of about 10.

Upon subjecting the so-formed tablets to a stability study at 40° C. for 18 months, it was found that the tablets including the pravastatin remained substantially stable; no lactone formation was observed.

EXAMPLE 6

A pravastatin formulation in the form of tablets, each containing 5 mg, 10 mg, 20 mg and 40 mg pravastatin, having the following composition was prepared as described below.

| Ingredient | Percent by Weight |
| --- | --- |
| Pravastatin | 10 |
| Lactose | 66.7 |
| Microcrystalline cellulose | 15 |
| Croscarmellose sodium | 2 |
| Magnesium stearate | 1 |
| Magnesium oxide | 3.3 |
| Polyvinylpyrrolidone | 2 |

Pravastatin, magnesium oxide, microcrystalline cellulose, and a fraction of the lactose were mixed for 5-10 minutes. The resulting mixture was passed through a #12 to #40 mesh screen. A portion of the croscarmellose sodium and the remaining lactose were added and mixing was continued for 5-10 minutes. The resulting mixture was granulated with an aqueous polyvinylpyrrolidone solution. The granulated wet mixture was passed through a #4 to #20 mesh screen and then dried in a tray drying oven. The dry granulation was passed through a #12-#20 mesh screen. The remainder of the croscarmellose sodium was added to the granules and mixed for 5-10 minutes. The magnesium stearate was added to the resulting granule mixture and mixing was continued for 1-5 minutes. The resulting formulation was compressed into tablets.

A dispersion of the tablets in water had a pH of about 10.

Upon subjecting the so-formed tablets to a stability study at 60° C. or 40° C./75% relative humidity for 2 months, it was found that the tablets including the pravastatin remained substantially stable; no lactone formation was observed.

EXAMPLE 7

A pravastatin formulation in the form of tablets, each containing 5 mg, 10 mg, 20 mg and 40 mg pravastatin, having the following composition was prepared as described in Example 6, except that FD&C Red #3 Lake color was mixed with pravastatin, magnesium oxide, microcrystalline cellulose and lactose.

| Ingredient | Percent by Weight |
| --- | --- |
| Pravastatin | 10 |
| Lactose | 66.5 |
| Microcrystalline cellulose | 15 |
| Croscarmellose sodium | 2 |
| Magnesium stearate | 1 |
| Magnesium oxide | 3.3 |
| FD&C Red #3 Lake | 0.2 |
| Polyvinylpyrrolidone | 2 |

A dispersion of the tablets in water had a pH of about 10.

Upon subjecting the so-formed tablets to a stability study at 60° C. or 40° C./75% relative humidity for 2 months, it was found that the tablets including the pravastatin remained substantially stable; no lactone formation was observed.

EXAMPLE 8

A pravastatin formulation in the form of tablets, each containing 5 mg, 10 mg, 20 mg and 40 mg pravastatin, having the following composition was prepared as described in Example 6, except that all of the croscarmellose sodium was mixed with dry granules prior to addition of magnesium stearate.

| Ingredient | Percent by Weight |
|---|---|
| Pravastatin | 10 |
| Lactose | 64.7 |
| Microcrystalline cellulose | 15 |
| Croscarmellose sodium | 5 |
| Magnesium stearate | 1 |
| Magnesium oxide | 3.3 |
| Polyvinylpyrrolidone | 1 |

A dispersion of the tablets in water had a pH of about 10.

Upon subjecting the so-formed tablets to a stability study at 60° C. or 40° C./75% relative humidity for 2 months, it was found that the tablets including the pravastatin remained substantially stable; no lactone formation was observed.

EXAMPLE 9

A pravastatin formulation in the form of tablets, having the following composition was prepared as described in Example 8 except that FD&C Red #3 Lake color was mixed with pravastatin, magnesium oxide, microcrystalline cellulose and lactose.

| Ingredient | Percent by Weight |
|---|---|
| Pravastatin | 10 |
| Lactose hydrous | 64.5 |
| Microcrystalline cellulose | 15 |
| Polyvinylpyrrolidone | 1 |
| Croscarmellose sodium | 5 |
| Magnesium stearate | 1 |
| Magnesium oxide | 3.3 |
| FD&C #3 Lake | 0.2 |

A dispersion of the tablets in water had a pH of about 10.

Upon subjecting the so-formed tablets to a stability study at 40 to 60° C. for several months, it was found that the tablets including the pravastatin remained substantially stable; no lactone formation was observed.

Other basifying agents may be employed which will raise the pH of an aqueous dispersion of the composition of the invention as shown in Examples 1 to 9 to about 10. Examples of such basifying agents include NaOH, KOH, Ca(OH)$_2$, Mg(OH)$_2$ or NH$_4$OH.

What is claimed is:

1. A stabilized pravastatin composition, which comprises pravastatin and one or more basifying agents, compatible with pravastatin, to impart a desired pH of at least 9 to an aqueous dispersion of said composition.

2. The pravastatin composition as defined in claim 1 wherein said pravastatin is present in an amount within the range of from about 1 to about 60% by weight of the composition.

3. The pravastatin composition as defined in claim 1 wherein the basifying agent is present in an amount within the range of from about 1 to about 75% by weight of the composition.

4. The pravastatin composition as defined in claim 1 wherein the basifying agent is an alkali metal hydroxide, an alkaline earth metal hydroxide or ammonium hydroxide.

5. The pravastatin composition as defined in claim 4 wherein the basifying agent is MgO, Mg(OH)$_2$, Ca(OH)$_2$, NaOH, KOH, LiOH, NH$_4$OH, Al(OH)$_3$ or magaldrate.

6. The pravastatin composition as defined in claim 1 in the form of a tablet.

7. A method of stabilizing pravastatin for storage, which comprises including with pravastatin one or more basifying agents, compatible with pravastatin, to impart a desired pH of at least 9 to an aqueous dispersion of the pravastatin.

8. The method as defined in claim 7 wherein the pravastatin is in the form of a pharmaceutical composition.

9. The method as claimed in claim 8 wherein said pravastatin is present in an amount within the range of from about 1 to about 60% by weight of the composition.

10. The method as defined in claim 8 the basifying agent is present in an amount within the range of from about 1 to about 75% by weight of the composition.

11. The method as defined in claim 8 wherein the basifying agent is an alkali metal hydroxide, an alkaline earth metal hydroxide or ammonium hydroxide.

12. The method as defined in claim 8 wherein the basifying agent is MgO, Mg(OH)$_2$, Ca(OH)$_2$, NaOH, KOH, LiOH, NH$_4$OH, Al(OH)$_3$ or magaldrate.

* * * * *